US008759324B2

(12) United States Patent
Spasojevic et al.

(10) Patent No.: US 8,759,324 B2
(45) Date of Patent: Jun. 24, 2014

(54) METHOD OF ACTIVATION OF OXAZAPHOSPHORINES

(71) Applicant: Duke University, Durham, NC (US)

(72) Inventors: Ivan Spasojevic, Durham, NC (US); Michael O. Colvin, Chapel Hill, NC (US); Ines Batinic-Haberle, Durham, NC (US); Susan M. Ludeman, Delmar, NY (US); Michael P. Gamcsik, Chapel Hill, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 13/763,085

(22) Filed: Feb. 8, 2013

(65) Prior Publication Data

US 2013/0172296 A1 Jul. 4, 2013

Related U.S. Application Data

(62) Division of application No. 12/375,482, filed as application No. PCT/US2007/023359 on Nov. 6, 2007, now Pat. No. 8,399,434.

(60) Provisional application No. 60/864,816, filed on Nov. 8, 2006.

(51) Int. Cl.
*A01N 57/00* (2006.01)
*A61K 31/675* (2006.01)

(52) U.S. Cl.
USPC .......................................... 514/90

(58) Field of Classification Search
CPC A61K 2300/99; A61K 31/555; A61K 31/675

USPC .......................................... 514/90
See application file for complete search history.

(56) References Cited

U.S. PATENT DOCUMENTS

| 5,281,616 A | 1/1994 | Dixon et al. |
| 5,744,158 A | 4/1998 | Mayer et al. |
| 5,810,888 A | 9/1998 | Fenn |
| 2002/0155999 A1 | 10/2002 | Han |

OTHER PUBLICATIONS

Stella VJ and Nti-Addae KW. Prodrug strategies to overcome poor water solubility. Advanced Drug Delivery Reviews. 2007; 59: 677-694.
Yang SJ et al. Epoxidation of olefins by a water-soluble iron(III) porphyrin complex and hydroperoxides in aqueous solution. Bull Korean Chem Soc. 1998; 19(3): 276-278.
International Search Report and Written Opinion, PCT/US07/23359, mailed Oct. 1, 2008.
Spasojević I et al. New approach to the activation of anti-cancer pro-drugs by metalloporphyrin-based cytochrome P450 mimics in all-aqueous biologically relevant system. Journal of Inorganic Biochemistry, 2006, 100: 1897-1092.

*Primary Examiner* — Anna Pagonakis
(74) *Attorney, Agent, or Firm* — Myers Bigel Sibley & Sajovec, P.A.

(57) ABSTRACT

The present invention provides a method of hydroxylating or oxidizing a compound of interest in a subject (e.g., a cytotoxic oxazaphosphorine prodrug), by administering the compound of interest to the subject; and concurrently administering the subject a metalloporphyrin in an amount effective to hydroxylate or oxidize the compound of interest in the subject.

7 Claims, 2 Drawing Sheets

METHOD OF ACTIVATION OF OXAZAPHOSPHORINES

RELATED APPLICATIONS

This application is a divisional of and claims priority to U.S. patent application Ser. No. 12/375,482, filed Jul. 20, 2009, which is a national phase application of PCT Application PCT/US2007/023359, filed Nov. 6, 2007, and published in English on Jun. 19, 2008, as International Publication No. WO 2008/073195, and which claims the benefit under 35 U.S.C. §119(e) of U.S. Provisional Patent Application Ser. No. 60/864,816, filed Nov. 8, 2006.

GOVERNMENT FUNDING

The present invention was made with government support under grant nos. 5-P30-CA14236-29 from the NIH/NCI, BC024326 from the DOD, and CA16783 from the NCI Public Health Services Department of Health and Human Services. The US Government has certain rights to this invention.

FIELD OF THE INVENTION

This invention concerns methods and formulations useful for the treatment of cancer in human and animal subjects in need thereof.

BACKGROUND OF THE INVENTION

Cyclophosphamide (CP), an oxazaphosphorine-type of cytotoxic pro-drug (including ifosfamide, mafosfamide, and trofosfamide), is the single most commonly utilized component in (i) conventional chemotherapy and (ii) high-dose chemotherapy/bone marrow transplant/stem-cell rescue regiments for cancer treatments [1-5]. The activation through the hydroxylation of CP by microsomal cytochrome P450 enzymes in liver, leads to 4-hydroxycyclophosphamide (4-OHCP) (FIG. 1), and ultimately to the formation of cytotoxic phosphoramide mustard which alkylates DNA, thus preventing the proliferation of tumor cells [1-5]. There are, however, side reactions on this pathway leading to the enzyme inactivation and toxic byproducts causing systemic toxicity. Thus, in order to increase the efficacy of the pro-drug at less toxic doses, it would be beneficial to localize the production of cytotoxic metabolites at the tumor site.

SUMMARY OF THE INVENTION

A first aspect of the present invention is a method of hydroxylating or oxidizing a compound of interest in a subject (e.g., a cytotoxic oxazaphosphorine prodrug), comprising: administering the compound of interest to the subject; and concurrently administering the subject a metalloporphyrin in an amount effective to hydroxylate or oxidize the compound of interest in the subject.

Stated otherwise, the present invention provides, in a method of treating a subject in need thereof with a cytotoxic oxazaphosphorine prodrug, the improvement comprising concurrently administering the subject a metalloporphyrin in an amount effective to enhance the efficacy of the oxazaphosphorine in the subject.

A further aspect of the invention is a pharmaceutical composition comprising, consisting of, or consisting essentially of: a cytotoxic oxazaphosphorine prodrug; a metalloporphyrin in an amount effective to enhance the efficacy of the oxazaphosphorine in a subject; and a pharmaceutically acceptable carrier.

A still further aspect of the present invention is the use of an active agent metalloporphyrin as described above for the preparation of a medicament for the treatment of a disorder as described above.

The present invention is explained in greater detail in the drawings herein and the specification set forth below.

Figure 1:
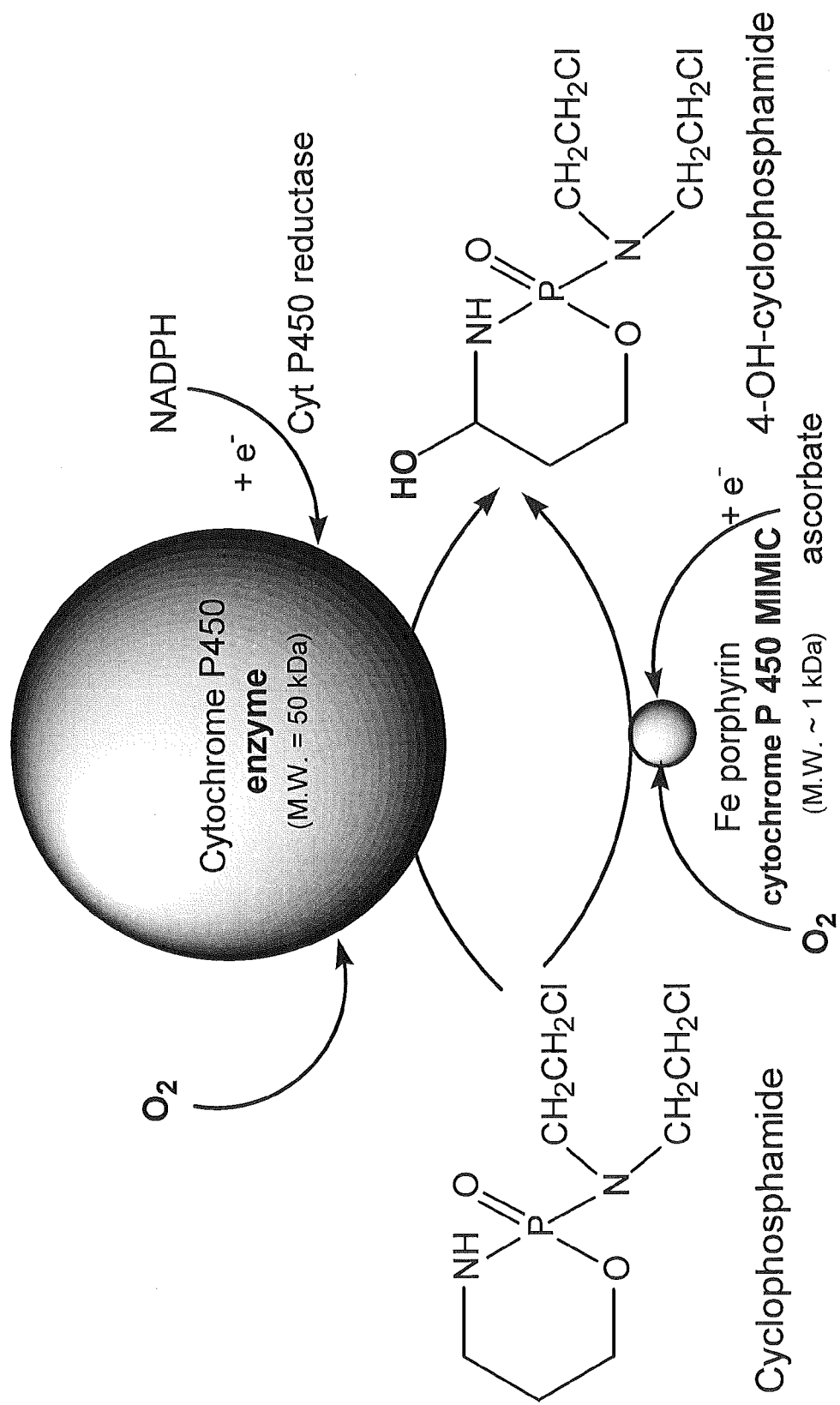
FIG. 1. Cytochrome P450 and Fe(III) porphyrin-catalyzed hydroxylation of cyclophosphamide.

The present invention is explained in greater detail in the following non-limiting Examples. The disclosures of all US Patent references cited herein are to be incorporated herein by reference in their entirety.

DETAILED DESCRIPTION OF PREFERRED EMBODIMENTS

"Cancer" as used herein includes any type of cancer, including but not limited to lung, colon, colorectal, liver, breast, prostate, ovarian, brain, and skin cancers or tumors.

"Autoimmune disease" as used herein includes any type of autoimmune disease, examples of which include but are not limited to arthritis, type 1 insulin-dependent diabetes mellitus, adult respiratory distress syndrome, inflammatory bowel disease, dermatitis, thrombotic thrombocytopenic purpura, Sjogren's syndrome, encephalitis, uveitis, leukocyte adhesion deficiency, rheumatoid arthritis, rheumatic fever, Reiter's syndrome, psoriatic arthritis, progressive systemic sclerosis, primary biliary cirrhosis, pemphigus, pemphigoid, necrotizing vasculitis, myasthenia gravis, multiple sclerosis, lupus erythematosus, polymyositis, sarcoidosis, granulomatosis, vasculitis, pernicious anemia, CNS inflammatory disorder, antigen-antibody complex mediated diseases, autoimmune haemolytic anemia, Hashimoto's thyroiditis, Graves disease, habitual spontaneous abortions, Reynard's syndrome, glomerulonephritis, dermatomyositis, chronic active hepatitis, celiac disease, tissue specific autoimmunity, degenerative autoimmunity delayed hypersensitivities, autoimmune complications of AIDS, atrophic gastritis, ankylosing spondylitis and Addison's disease. See, e.g., U.S. Pat. No. 6,984,625.

The term "treat" as used herein refers to any type of treatment that imparts a benefit to a patient afflicted with a disease, including improvement in the condition of the patient (e.g., in one or more symptoms), delay in the progression of the disease, etc.

The term "pharmaceutically acceptable" as used herein means that the compound or composition is suitable for administration to a subject to achieve the treatments described herein, without unduly deleterious side effects in light of the severity of the disease and necessity of the treatment.

As used herein, the administration of two or more compounds "concurrently" means that the two compounds are administered closely enough in time that the presence of one alters the biological effects of the other. The two compounds may be administered simultaneously or sequentially. Simultaneous administration may be carried out by mixing the compounds prior to administration, or by administering the compounds at the same point in time but at different anatomic sites and/or by using different routes of administration.

The present invention is primarily concerned with the treatment of human subjects, but the invention may also be carried out on animal subjects, particularly mammalian subjects such as mice, rats, dogs, cats, livestock and horses for veterinary purposes, and for drug screening and drug development purposes.

1. Active Compounds.

The present invention employs oxazaphosphorine active compounds in combination with metallic porphyrin active compounds.

Oxazaphosphorines that may be used to carry out the present invention are known. Examples include cyclophosphamides, which in turn include cyclophosphamide and derivatives and analogs thereof which are effective as a cancer chemotherapeutic agent through essentially the same mechanism or mode of action as cyclophosphamide. See, e.g., U.S. Pat. No. 6,268,138. Examples of such analogs and derivatives include but are not limited to ifosfamide, maphosphamide, and trofosfamide. Additional examples are disclosed in U.S. Pat. Nos. 6,187,941; 5,190,929; 4,770,870; and 4,716,242, the disclosures of which are incorporated by reference herein in their entirety.

Metalloporphyrins that may be used to carry out the present invention are known. Numerous examples are available in the literature on porphyrins used in catalysis (see, e.g. References 12-40 herein) and the literature on porphyrins used in photodynamic therapy. Examples include but are not limited to those described in U.S. Pat. Nos. 7,087,214; 7,067,653; 6,995,260; 6,953,570; 6,777,402; 6,573,258; 6,147,207; 5,770,619; 5,424,305; 5,214,036; and 5,053,423. Where particular metals are described as the coordinated metal in the porphyrins shown in the foregoing, those skilled in the art will appreciate that other metals can be substituted in place thereof, with iron, manganese, cobalt, nickel, ruthenium, and copper currently preferred. Preferably the metalloporphyrin is selected to catalyze the hydroxylation of the concurrently administered oxazaphosphorazine. Thus the term "metalloporphyrin" is herein intended to include transition metal (III)-substituted macrocyclic ligand complexes such as metal (III) complexes with substituted porphyrin and substituted porphyrin analogues such as are porphyrazine, texaphyrin, N-confused porphyrin and corrole. "Substituted macrocyclic ligand" is meant to include and not be limited to substituted porphyrins, porphyrazines, texaphyrins, and corroles. The substituted macrocyclic ligands of the presently disclosed subject matter include, for example, ortho-, meta- and para-tetrakis N-substituted porphyrins. The substituted macrocyclic ligands of the presently disclosed subject matter include, for example, those compounds disclosed in WO 2005/077269 A1, U.S. Pat. No. 6,916,799 B2, U.S. Pat. No. 6,544,975 B1, International Publication No. WO 00/075144 A3, International Publication No. WO 2005/097123 A3 and Patent Application Publication No. US 2007/0072825 A1, all of which are herein incorporated by reference in their entirety. Thus in some embodiments the metalloporphyrin is selected from the group consisting of a substituted porphyrin, porphyrazine, texaphyrin, and corrole. Particular examples include those wherein the substituted porphyrin is an ortho-, meta- or para-tetrakis N-substituted porphyrin. More particular examples include those wherein the ortho-, meta- or para-tetrakis N-substituted porphyrin is an ortho-tetrakis N-alkylpyridinium porphyrin, wherein the alkyl has from 1-8 $CH_2$ groups. More particular examples include those wherein the ortho-tetrakis N-alkylpyridinium porphyrin is an ortho-tetrakis(N-ethylpyridinium-2-yl])porphyrin or an ortho-tetrakis (N-hexylpyridinium-2yl)porphyrin. Still more particular examples include those wherein the ortho-, meta- or para-tetrakis N-substituted porphyrin is selected from the group consisting of a tetrakis di(N,N')-alkylimidazolium porphyrin, a tetrakis di(N,N')-alkylpyrazolium porphyrin, a tetrakis di(N,N')-alkylpyrimidinium porphyrin, a tetrakis di(N,N')-alkylpyrazinium porphyrin and a tetrakis di(N,N')-alkylpyridazinium porphyrin, wherein the alkyl has from 1-8 $CH_2$ groups.

The term "pharmaceutically acceptable prodrugs" as used herein refers to those prodrugs of the compounds of the present invention which are, within the scope of sound medical judgment, suitable for use in contact with the tissues of humans and lower animals without undue toxicity, irritation, allergic response and the like, commensurate with a reasonable risk/benefit ratio, and effective for their intended use, as well as the zwitterionic forms, where possible, of the compounds of the invention. The term "prodrug" refers to compounds that are rapidly transformed in vivo to yield the parent compound of the above formulae, for example, by hydrolysis in blood. A thorough discussion is provided in T. Higuchi and V. Stella, Prodrugs as Novel delivery Systems, Vol. 14 of the A.C.S. Symposium Series and in Edward B. Roche, ed., Bioreversible Carriers in Drug Design, American Pharmaceutical Association and Pergamon Press, 1987, both of which are incorporated by reference herein. See also U.S. Pat. No. 6,680,299 Examples include a prodrug that is metabolized in vivo by a subject to an active drug having an activity of active compounds as described herein, wherein the prodrug is an ester of an alcohol or carboxylic acid group, if such a group is present in the compound; an acetal or ketal of an alcohol group, if such a group is present in the compound; an N-Mannich base or an imine of an amine group, if such a group is present in the compound; or a Schiff base, oxime, acetal, enol ester, oxazolidine, or thiazolidine of a carbonyl group, if such a group is present in the compound, such as described in U.S. Pat. No. 6,680,324 and U.S. Pat. No. 6,680,322.

The active compounds disclosed herein can be prepared in the form of their pharmaceutically acceptable salts. Pharmaceutically acceptable salts are salts that retain the desired biological activity of the parent compound and do not impart undesired toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; (b) salts formed from elemental anions such as chlorine, bromine, and iodine, and (c) salts derived from bases, such as ammonium salts, alkali metal salts such as those of sodium and potassium, alkaline earth metal salts such as those of calcium and magnesium, and salts with organic bases such as dicyclohexylamine and N-methyl-D-glucamine.

2. Pharmaceutical Formulations.

The active compounds described above may be formulated for administration in a pharmaceutical carrier in accordance with known techniques. See, e.g., Remington, *The Science And Practice of Pharmacy* ($9^{th}$ Ed. 1995). In the manufacture of a pharmaceutical formulation according to the invention, the active compound (including the physiologically acceptable salts thereof) is typically admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation, for example, a tablet, which may contain from 0.01 or 0.5% to 95% or 99% by weight of the active compound. One or more active compounds may be incorporated in the formulations of the invention, which may be prepared by any of the well known techniques of pharmacy comprising admixing the components, optionally including one or more accessory ingredients.

The formulations of the invention include those suitable for oral, rectal, topical, buccal (e.g., sublingual), vaginal, parenteral (e.g., subcutaneous, intramuscular, intradermal, or intravenous), topical (i.e., both skin and mucosal surfaces, including airway surfaces) and transdermal administration, although the most suitable route in any given case will depend on the nature and severity of the condition being treated and on the nature of the particular active compound which is being used.

Preferred routes of parenteral administration include intrathecal injection, including directly into the tumor, and intraventricular injection into a ventricle of the brain.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above). In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Formulations suitable for buccal (sublingual) administration include lozenges comprising the active compound in a flavoured base, usually sucrose and acacia or tragacanth; and pastilles comprising the compound in an inert base such as gelatin and glycerin or sucrose and acacia.

Formulations of the present invention suitable for parenteral administration comprise sterile aqueous and non-aqueous injection solutions of the active compound, which preparations are preferably isotonic with the blood of the intended recipient. These preparations may contain anti-oxidants, buffers, bacteriostats and solutes which render the formulation isotonic with the blood of the intended recipient. Aqueous and non-aqueous sterile suspensions may include suspending agents and thickening agents. The formulations may be presented in unit\dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described. For example, in one aspect of the present invention, there is provided an injectable, stable, sterile composition comprising a compound of the invention, or a salt thereof, in a unit dosage form in a sealed container. The compound or salt is provided in the form of a lyophilizate which is capable of being reconstituted with a suitable pharmaceutically acceptable carrier to form a liquid composition suitable for injection thereof into a subject. The unit dosage form typically comprises from about 10 mg to about 10 grams of the compound or salt. When the compound or salt is substantially water-insoluble, a sufficient amount of emulsifying agent which is physiologically acceptable may be employed in sufficient quantity to emulsify the compound or salt in an aqueous carrier. One such useful emulsifying agent is phosphatidyl choline.

Formulations suitable for rectal administration are preferably presented as unit dose suppositories. These may be prepared by admixing the active compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include petroleum jelly, lanoline, polyethylene glycols, alcohols, transdermal enhancers, and combinations of two or more thereof.

Formulations suitable for transdermal administration may be presented as discrete patches adapted to remain in intimate contact with the epidermis of the recipient for a prolonged period of time. Formulations suitable for transdermal administration may also be delivered by iontophoresis (see, for example, *Pharmaceutical Research* 3 (6):318 (1986)) and typically take the form of an optionally buffered aqueous solution of the active compound. Suitable formulations comprise citrate or bis\tris buffer (pH 6) or ethanol/water and contain from 0.1 to 0.2M active ingredient.

Further, the present invention provides particulate formulations in which the active agent (or salt thereof) is encapsulated in or incorporated into a biodegradable particle, liposome or lipid vesicle, nanoparticle or the like. Techniques for forming such particulate formulations are known in the art. For example, when the compound or salt thereof is an aqueous-soluble salt, using conventional formulation technology, the same may be incorporated into particles such as lipid vesicles. In such an instance, due to the water solubility of the compound or salt, the compound or salt will be substantially entrained within the center or core of a particle such as a liposome. The lipid layer employed may be of any conventional composition and may either contain cholesterol or may be cholesterol-free. When the compound or salt of interest is water-insoluble, again employing conventional formation technology, the salt may be substantially entrained within the hydrophobic lipid bilayer which forms the structure of the liposome, or other particle space. In either instance, the particles which are produced may be reduced in size, as through the use of standard sonication and homogenization techniques.

Of course, the particulate and/or liposomal formulations containing the compounds disclosed herein or salts thereof, may be lyophilized to produce a lyophilizate which may be reconstituted with a pharmaceutically acceptable carrier, such as water, to regenerate a particulate and/or liposomal suspension.

Other pharmaceutical compositions may be prepared from the water-insoluble compounds disclosed herein, or salts thereof, such as aqueous base emulsions. In such an instance, the composition will contain a sufficient amount of pharmaceutically acceptable emulsifying agent to emulsify the desired amount of the compound or salt thereof. Particularly useful emulsifying agents include phosphatidyl cholines, and lecithin.

In addition to active compounds, the pharmaceutical compositions may contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the compositions may contain microbial preservatives. Useful microbial preservatives include methylparaben, propylparaben, and benzyl alcohol. The microbial preservative is typically employed when the formulation is placed in a vial designed for multidose use. Of course, as indicated, the pharmaceutical compositions of the present invention may be lyophilized using techniques well known in the art.

3. Dosage and Routes of Administration.

As noted above, the present invention provides pharmaceutical formulations comprising the active compounds, separately or in combination (including the pharmaceutically acceptable salts thereof), in pharmaceutically acceptable carriers for oral, rectal, topical, buccal, parenteral injection (e.g., intramuscular, intradermal, intravenous, intraarterial), and transdermal administration.

Routes of parenteral administration include intratumoral injection, intrathecal injection (including directly into a brain tumor), and intraventricular injection into a ventricle of the brain.

The therapeutically effective dosage of any specific compound, the use of which is in the scope of present invention, will vary somewhat from compound to compound, and patient to patient, and will depend upon the condition of the patient and the route of delivery. As a general proposition, a dosage from about 0.1 to about 50 mg/kg will have therapeutic efficacy, with all weights being calculated based upon the weight of the active compound, including the cases where a salt is employed. Toxicity concerns at the higher level may restrict intravenous dosages to a lower level such as up to about 10 mg/kg, with all weights being calculated based upon the weight of the active base, including the cases where a salt is employed. A dosage from about 10 mg/kg to about 50 mg/kg may be employed for oral administration. Typically, a dosage from about 0.5 mg/kg to 5 mg/kg may be employed for intramuscular injection. Preferred dosages are 1 µmol/kg to 50 µmol/kg, and more preferably 22 µmol/kg and 33 µmol/kg of the compound for intravenous or oral administration. The duration of the treatment is usually once per day for a period of two to three weeks or until the condition is essentially controlled. Lower doses given less frequently can be used prophylactically to prevent or reduce the incidence of recurrence of the infection.

It also is conceivable that more than one administration of either an active compound of the invention, or the other agent will be desired. In this regard, various combinations may be employed. By way of illustration, where the active compound is "A" and the other agent is "B", the following permutations based on 3 and 4 total administrations are exemplary:

A/B/A B/A/B B/B/A A/A/B B/A/A A/B/B B/B/B/A B/B/A/B

A/A/B/B A/B/A/B A/B/B/A B/B/A/A B/A/B/A B/A/A/B B/B/B/A

A/A/A/B B/A/A/A A/B/A/A A/A/B/A A/B/B/B B/A/B/B B/B/A/B

Other combinations are likewise contemplated.

The present invention is explained in greater detail in the following non-limiting Examples.

EXAMPLE 1

This invention aims at developing suitable low-molecular weight substitute for the cytochrome P450 enzyme with the ultimate goal to deliver it directly to the tumor thus producing the active metabolite 4-OHCP locally at high concentrations but at low systemic levels. For this purpose we utilize metalloporphyrins which exhibit high metal-ligand stability and redox activity.

Metalloporphyrin (MP) constitutes the active site of numerous enzymes (hemoglobin, myoglobin, cytochromes, chlorophyll, guanylate cyclase, catalase, peroxidase, nitric oxide synthase, vitamin $B_{12}$, chlorophyll, etc), due to: (a) the ability of the metal center to bind oxygen ($O_2$) and other small molecules (CO, NO, $H_2O$), as well as many protein amino acid residues (cysteine, methionine, histidine, etc) and (b) the electron transfer (redox) properties of the metal, i.e. the ability to accept and donate electrons thus acting as a catalyst [6-8].

In a laboratory setting, the core structure of the porphyrin ligand can be modified to alter the chemical and redox properties of the metal center as well as the solubility and bulkiness of the whole molecule [6-9]. Synthetically prepared metalloporphyrins, highly stable low-molecular-weight molecules capable of catalyzing electron-transfer reactions, have been successfully utilized in industrial catalysis, as imaging contrast agents, in photodynamic therapy [10, 11] and as biological catalysts—enzyme mimics [12-20]. Both the Fe and Mn porphyrins have been studied as mimics of cytochrome P450 in oxidation, epoxidation, and hydroxylation in the presence of oxidants [21-31] and reductants/excess oxygen either in organic or biphasic systems [32-38]. Mimicking cytochrome P450-catalyzed dehydration [39] and cytochrome P450 reductase activity have been reported also [40].

To the best of our knowledge, the work presented here is the first study where low-molecular weight water-soluble metalloporphyrins have been employed as catalysts (mimics of liver cytochrome P450 enzymes) in an anti-cancer drug activation reaction, in an all-aqueous biologically relevant medium without additional oxidant and with cellular reductant ascorbate as a source of electrons (instead of NADPH in the case of cytochrome P450), under concentrations similar to those found in vivo [41].

EXPERIMENTAL

Abbreviations

The following abbreviations are used herein: MP, metalloporphyrin; $Fe^{III}T(2,6-F_2-3-SO_3-P)P^{3-}$, Fe(III) meso tetrakis(2,6-difluoro-3-sulfonatophenyl)porphyrin; $Fe^{III}T(2,6-Cl_2-3-SO_3-P)P^{3-}$, Fe(III) meso tetrakis(2,6-dichloro-3-sulfonatophenyl)porphyrin; $Fe^{III}TBAP^{3-}$, also abbreviated as $Fe^{III}TCPP^{3-}$, Fe(III) meso tetrakis(4-carboxylatophenyl)porphyrin; $Fe^{III}PP-IX^-$, Fe(III) protoporphyrin IX; $Fe^{III}TM-2-PyP^+$, Fe(III) tetrakis(N-methylpyridinium-2-yl)porphyrin; $Mn^{III}TM-2-PyP^{5+}$, Mn(III) tetrakis(N-methylpyridinium-2-yl)porphyrin; $Mn^{III}TM-3-PyP^{5+}$, Mn(III) tetrakis(N-methylpyridinium-3-yl)porphyrin; CP, cyclophosphamide; 4-OHCP, 4-hydroxycyclophosphamide; NHE, normal hydrogen electrode; PBS, phosphate-buffered saline.

Materials. We employed two electron-deficient anionic Fe(III) meso tetrakis(2,6-difluoro-3-sulfonatophenyl)porphyrin (Fe$^{III}$T(2,6-F$_2$-3-SO$_3$—P)P$^{3-}$), and Fe(III) meso tetrakis(2,6-dichloro-3-sulfonatophenyl)porphyrin (Fe$^{III}$T(2,6-Cl$_2$-3-SO$_3$—P)P$^{3-}$), and two electron-rich anionic Fe(III) meso tetrakis(4-carboxyphenyl)porphyrin (Fe$^{III}$TBAP$^{3-}$, also abbreviated as Fe$^{III}$TCPP$^{3-}$) and Fe(III) protoporphyrin IX (Fe$^{III}$PP-IX$^-$) (Scheme I). All porphyrins were obtained from MidCentury Chemicals, Chicago, Ill. (Scheme I). Also, the electron-deficient cationic Fe(III) meso tetrakis(N-methylpyridinium-2-yl)porphyrin), Fe$^{III}$TM-2-PyP$^{5+}$, and its Mn(III) isomeric analogues, Mn$^{III}$TM-2-PyP$^{5+}$ and Mn$^{III}$-iTM-3-PyP$^{5+}$, prepared as previously described, were studied [42, 42]. Although of extremely high metal-ligand stability when its metal center is in the +3 oxidation state, a metalloporphyrin may lose metal if metal center is reduced to the +2 state in reducing cellular environment [42, 43]. To study the possible effects of free metal on the hydroxylation of cyclophosphamide, the metal salts FeCl$_3$ (FeCl$_3$×6H$_2$O, Mallinckrodt) and MnCl$_2$ (MnCl$_2$×4 H$_2$O, J. T. Baker) were used as controls. Cyclophosphamide, D-mannitol, and sodium L-ascorbate were from Sigma, PBS was from Gibco and H$_2$O$_2$ (30% solution) was from Mallinckrodt. The o-(2,3,4,5,6-pentafluorobenzyl)hydroxylamine hydrochloride was obtained from Lancaster Synthesis.

Methods

The electrochemistry was done as previously described [42, 43] on CH Instruments 600 Voltammetric Analyzer. The metal-centered redox potentials of aquametalloporhyrins were measured in 0.1 M NaCl and 0.01 M HCl. The anionic porphyrins, FeTBAP$^{3-}$ and FePP-IX$^-$ precipitate under acidic conditions when carboxylates are protonated [42]. Thus, their voltammograms were obtained in 0.1 M NaCl, 0.1 M 1-methylimidazole, 0.05 M phosphate buffer, pH 7.8. Scan rates were 0.1 V/s. The potentials were standardized against MnTE-2-PyP$^{5+}$ and are given in Table 1, in mV versus normal hydrogen electrode, NHE [42].

Hydroxylation reaction was followed in phosphate-buffered saline (PBS) at pH 5.5 and 7.4 and at 37° C. with 10 μM Fe and Mn porphyrins, 2 mM ascorbate and 1 mM cyclophosphamide, under aerobic conditions (0.21 mM O$_2$). The reaction was stopped by dilution with organic solvents and the hydroxylation product 4-OHCP was trapped overnight by a hydroxylamine forming a stable aldophosphamide oxime derivative as reported [4]. The oxime was subsequently measured by GC/MS as previously described [4].

Scheme I. Metalloporphyrins studied.

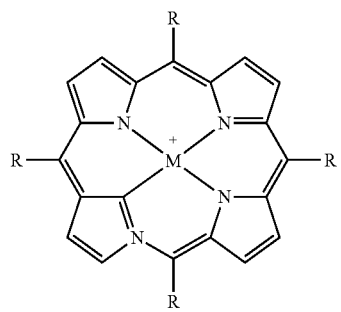

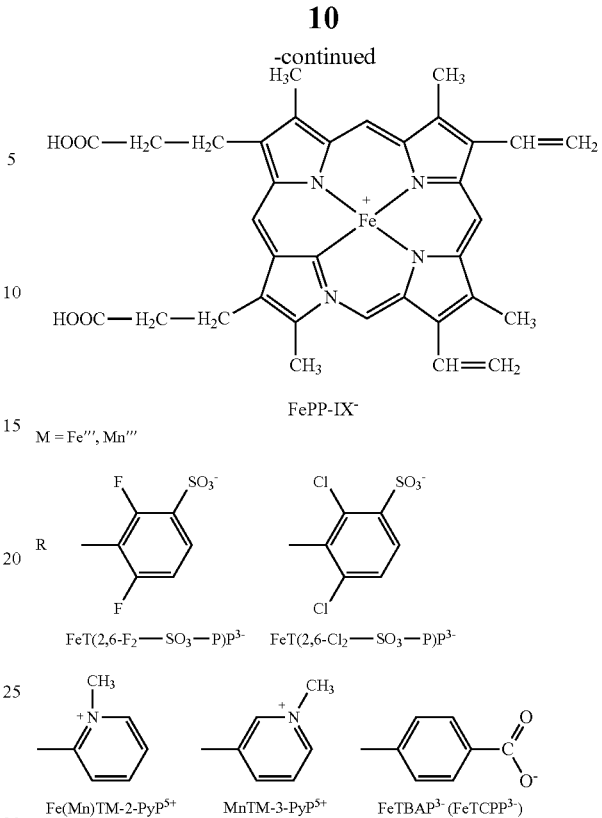

TABLE 1

The metal-centered redox potential of aquametalloporhyrins are done in 0.1M NaCl and 0.01 M HCl, and of FeTBAP$^{3-}$ and FePP-IX$^-$ were done in 0.1 M NaCl, 0.1 M 1-methylimidazole, 0.05 M phosphate buffer, pH 7.8. Scan rates were 0.1 V/s. Errors are ±3 mV. Charges were omitted when respective redox couples were indicated. M is either iron or manganese.

| Metalloporphyrin | E$_{1/2}$, mV vs NHE | | |
|---|---|---|---|
| | (H$_2$O)M$^{III}$P/ (H$_2$O)M$^{II}$P | (OH)M$^{III}$P/ (H$_2$O)M$^{II}$P | (1-MeIm)$_2$M$^{III}$P/ (1-MeIm)$_2$M$^{II}$P |
| FeT(2,6-F$_2$-3-SO$_3$P)P$^{3-}$ | +124 | +74$^a$ | +114$^a$ |
| FeT(2,6-Cl$_2$-3-SO$_3$P)P$^{3-}$ | +144 | +94$^b$ | +134$^b$ |
| FeTM-2-PyP$^{5+a}$ | +355$^b$ | +212$^b$ | +432$^b$ |
| FeTBAP$^{3-}$ | | | +22 |
| FePPIX$^-$ | 112 | | — |
| MnTM-2-PyP$^{5+a}$ | +220$^b$ | +128$^b$ | |
| MnTM-3-PyP$^{5+a}$ | +52$^b$ | +42$^c$ | |
| Fe$^{III}$/Fe$^{II\,b}$ | +771$^d$ | | |
| Mn$^{III}$/Mn$^{II\,b}$ | +1541$^d$ | | |

$^a$data estimated based on the existing potentials of difluoro- and dichloro analogues [42] and those obtained herein. The di-ortho-substituted porphyrins are fairly insensitive to axial ligation due to the steric hindrance when compared to the mono-ortho porphyrins.
$^b$ref 42, data obtained at pH 7.8, 0.05 M phosphate buffer, 0.1M NaCl, 0.5 mM porphyrin.
$^c$ref 62, data obtained at pH 11 where only 33% of the (OH)MnTM-3-PyP$^{4+}$ exists; pK$_a$ of the axial water is 11.5$^{(17)}$).
$^d$ref 63.

Generally, the synthetic antioxidants are prone to undergo oxidative degradation, which limits their catalytic efficacy. That in turns makes a design of robust catalyst quite a challenge. The stability of metalloporphyrins with respect to oxidative degradation was followed on Shimadzu UV-2501PC spectrophotometer under aerobic conditions similar to those previously reported [43, 49]: 10 μM porphyrins, 2 mM ascorbic acid, 0.26 mM O$_2$, at 25° C. and in PBS, at pH 7.4 where both cationic and anionic porphyrins were soluble [42] and in the presence and absence of 1 mM cyclophosphamide. In addition, the time-dependent spectra and time-dependent change in absorbance at 417.5 nm ((H$_2$O)Fe$^{III}$TM-2-PyP$^{4+}$) were followed with 9 μM (OH)Fe$^{III}$TM-2-PyP$^{5+}$, 2 mM ascorbic acid, +/−50 μM H$_2$O$_2$, +/−50 mM mannitol (scavenger of .OH radical), in PBS, pH 7.4, under aerobic conditions (0.26 mM O$_2$) at 25° C. (data not shown). We have chosen FeTM-2-PyP$^{5+}$ based on the study of Almarsson and Bruice [50] which showed that with multianionic and multicationic porphyrins, the charge surrounding iron metal center seems not to greatly influence the reaction of iron porphyrins with alkylhydroperoxides.

All experiments were performed in triplicate.

Results and Discussion.

Figure 2:
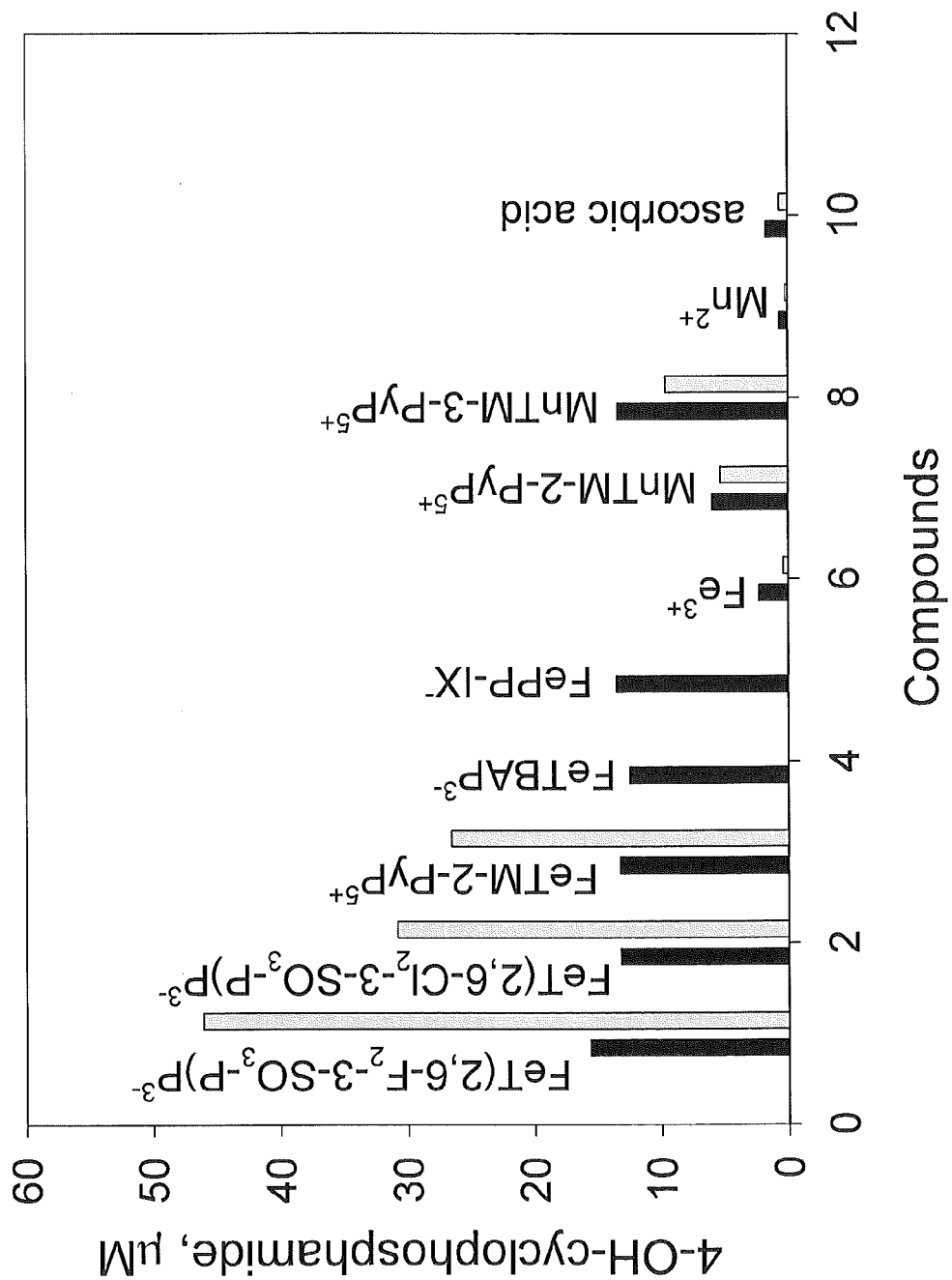
FIG. 2. The hydroxylation of 1 mM cyclophosphamide at 6 hours by 10 μM metalloporphyrins and corresponding metal chlorides in the presence of 2 mM ascorbate, in PBS at pH 7.4 (black bars), and pH 5.5 (gray bars) at 37° C. under aerobic conditions (0.26 mM oxygen). Errors are ±2%.

A catalytic acceleration of the hydroxylation occurred at 37° C. after the addition of 10 μM Fe(III) and Mn(III) porphyrins into the incubation mixture containing 1 mM cyclophosphamide, 2 mM ascorbate and phosphate-buffered saline PBS (pH 7.4) (FIG. 2). Cyclophosphamide alone, without metalloporphyrin or ascorbate present, did not produce 4-OHCP. Also, metalloporphyrins alone did not cause any CP hydroxylation. In the absence of metalloporphyrin, ascorbic acid, itself, underwent slow reaction with oxygen [44], leading to very low yields (FIG. 2). The similar level of hydroxylation was observed with MnCl$_2$ in the presence of ascorbic acid and may thus be ascribed to the effect of ascorbic acid alone. FeCl$_3$ was only slightly better than the ascorbic acid alone in hydroxylating cyclophosphamide, which suggests a weak catalytic action of free iron.

A pH effect was observed with difluoro-, dichloroporphyrin and FeTM-2-PyP$^{5+}$; the yield of 4-OHCP increased up to 3-fold in a pH 5.5 medium (FIG. 2) where 10 μM FeT-2,6-F$_2$-3-SO$_3$—P$^{3-}$ hydroxylated ~5-fold more of cyclophosphamide. The pK$_a$ values for the axially ligated water vary between 5.5 for the electron-deficient and 7.0 for the electron-rich Fe(III) porphyrins [43]. At lower pH, the aquairon(III) species predominates, and with higher E$_{1/2}$ (Table 1) it is more readily reducible than the monohydroxoiron(III) species [42]. Consequently, a certain level of favorable selectivity is expected in the production of 4-OHCP in tumor, whose extracellular pH was reported to be as low as 5.2, when compared to normal tissue (pH~7.3) [45-48]. Moreover, near the surface of macrophages, which may comprise up to 50% of the tumor mass, the pH may be as low as 3.6 [45-48]. At pH 5.5 where ~50% of carboxylate groups of FePP-IX$^-$ and FeTBAP$^{3-}$ (pK$_a$ are ~5) are protonated, both porphyrins precipitate out of the solutions. Thus no pH effect has been assessed with these two porphyrins. Due to the weak axial interactions that dominate the chemistry of Mn porphyrins [42 and refs therein], they exist in the form of aquamanganese (III) porphyrin species in a wide range of pH=0-9 [42] and are thus insensitive to a pH change from 7.4 to 5.5 (FIG. 2).

We have previously observed that aerobically, in the presence of excess ascorbic acid over oxygen, Mn porphyrins are reduced at the metal center (followed by a corresponding change in uv/vis spectra) and then undergo further uv/vis spectral change [42, 49] which is qualitatively identical to the change observed upon their exposure to H$_2$O$_2$ [42]. Time-dependent spectra and kinetic traces (data not shown) observed in this work with Fe$^{III}$TM-2-PyP$^{5+}$/ascorbate system (PBS, pH 7.4) were essentially the same whether H$_2$O$_2$ or mannitol (an .OH scavenger) were added or not. The (OH)Fe$^{III}$TM-2-PyP$^{4+}$ species, with Soret band at 408 nm, was reduced by ascorbic acid to (H$_2$O)Fe$^{II}$TM-2-PyP$^{4+}$ which had Soret band at 417.5 nm. The 417.5 nm band did not shift upon the addition of either mannitol or H$_2$O$_2$. The absorbance at 417.5 nm decreased slowly (indicating porphyrin degradation), and at nearly identical rates whether mannitol or H$_2$O$_2$ were present in the system (data not shown). That suggests that H$_2$O$_2$, whether added to the system or produced endogenously by the reduction of Fe-bound oxygen, is a key species involved in porphyrin degradation which is in competition with hydroxylation. The lack of effect of mannitol indicates that O=Fe$^{IV}$P.$^+$ is hydroxylating cyclophosphamide rather than freely diffusing .OH. Our data are best accommodated by the studies of Almarsson and Bruice [50], Murata et al [51] and Panicucci and Bruice [52]. The initial oxygen binding to the ascorbate-reduced Fe$^{II}$ porphyrin center generates O$_2$.$^-$—Fe$^{III}$P, which is further reduced to Fe(III) hydroperoxo species similar to cytochrome P450 [12]. Fe(III) hydroperoxo species undergoes O—O homolysis, leading to the solvent caged intermediates [H$_3$O$^+$, O=Fe$^{IV}$P, .OH], followed by 1e$^-$ oxidation of O=Fe$^{IV}$P by .OH to yield O=Fe$^{IV}$P.$^+$, the latter species being thermodynamically favored in aqueous solution [52].

The destruction ("bleaching") of the porphyrin is a serious problem encountered in all studies of metalloporphyrin-based catalysis. Even the oxidative damage of hemoglobin has been recently reported [60]. We observed bleaching in the cases of all metalloporphyrins studied. Under the same experimental conditions as in catalysis experiments (pH 7.4), the degradation of metalloporphyrins was followed spectrophotometrically. The most potent catalysts, difluoro- and dichloroporphyrins were the least stable. In the presence of cyclophosphamide, after 6 hours the remaining fractions were: 19% of FeT(2,6-F$_2$-3-SO$_3$P)P$^-$, 23% of FeT(2,6-Cl$_2$-3-SO$_3$P)P$^{3-}$, 24% of FeTBAP$^{3-}$, 41% of FeTM-2-PyP$^{5+}$, 71% of FePP-IX$^-$, 91% of MnTM-2-PyP$^{5+}$ and 94% of MnTM-3-PyP$^{5+}$. All porphyrins were more stable in the presence than in the absence [42, 43, 49] of the substrate, cyclophosphamide. Thus, modulating the susceptibility of the metalloporphyrins to oxidation is important to maximize their catalytic potency/lifetime ratio.

Although difluoro- and dichloroporphyrins have similar E$_{1/2}$ values (Table 1), the difluoroporphyrin proved to be the more effective catalyst in our studies. Steric hindrance in the case of the FeT(2,6-Cl$_2$-3-SO$_3$P)P$^{3-}$, due to the bulky chlorine atoms in ortho positions, may account for its lower efficacy relative to the difluoro analogue (FIG. 2). FeTM-2-PyP$^{5+}$ is less potent than difluoro- and dichloroporphyrin. The more positive E$_{1/2}$ of FeTM-2-PyP$^{5+}$ (Table 1) stabilizes it in the Fe +2 oxidation state, which does not favor reoxidation by oxygen, thus lowering its hydroxylation power. However, its stability to bleaching partly compensates for its lower efficacy. Along this line, FePP-IX$^-$ is stabilized in the Fe +3 oxidation state, and is consequently very resistant to bleaching. FeTBAP$^{3-}$ with a more positive E$_{1/2}$ than FePP-IX$^-$ is a more effective catalyst but again it is more prone to destruction. Mn porphyrins, MnTM-2-PyP$^{5+}$ and MnTM-3-PyP$^{5+}$ do not favor axial binding of the oxygen upon reduction and are thus inferior as catalysts to their Fe(III) analogue FeTM-2-PyP$^{5+}$[42]. The meta isomer, MnTM-3-PyP$^{5+}$ (E$_{1/2}$=+52 mV vs NHE) is more susceptible to the reoxidation than ortho isomer MnTM-2-PyP$^{5+}$ (E$_{1/2}$=+228 mV vs NHE) which explains its higher catalytic potency (FIG. 2). It should be noted that the redox potential for the O=Mn$^{IV}$P/Mn$^{III}$P redox couple is insensitive to the electron-deficiency/richness of the Mn porphyrin and consequently does not correlate with the observed differences in catalytic potency [42 and refs therein].

The yield of 4-OHCP obtained with FeT(2,6-F$_2$-3-SO$_3$P) P$^{3-}$/ascorbate approximates well the yield obtained with cyt P450 enzymes in vivo. Thus, with 1 mM CP the 46.11 μM 4-OHCP was produced at pH 5.5, i.e. the yield was 4.6%. At pH 7.4 the 15.62 µM 4-OHCP was formed, i.e. the yield was 1.6% (FIG. 2). The cyclophosphamide concentration (1 mM) in our system equals those administered to patients (1.1 g) [5]. Based on the reported plasma data, after intravenous administration of 1.1 g of CP [5], around 2.4% of CP was hydroxylated to 4-OHCP (0.69 µg/mL) at the peak CP levels (27.58 µg/mL µM).

In conclusion, the usefulness of a metalloporphyrin as cytochrome P450 mimic would depend upon the combined effects of: (a) the optimal metal-centered redox potential for the $M^{III}P/M^{II}P$ redox couple, i.e. reducibility of $M^{III}P$; (b) the oxygen binding affinity of the $M^{II}P$ species which is influenced by steric and electrostatic factors; and (c) the susceptibility of the catalyst towards oxidative degradation.

REFERENCES

1. G. Zon, S. M. Ludeman, J. A. Brandt, V. L. Boyd, G. Ozkan, W. Egan, K.-L. Shao, J. Med. Chem. 27 (1984) 466-485.
2. S. M. Ludeman, Curr. Pharm. Design 5 (1999) 627-643.
3. F. Baumann, R. Preiss, J. Chromatogr. B 764 (2001) 173-192.
4. L. W. Anderson, S. M. Ludeman, O. M. Colvin, L. B. Grochow, J. M. Strong, J. Chromatogr. B 667 (1995) 247-257.
5. F. Baumann, C. Lorenz, U. Jaehde, R. Preiss, J. Chromatogr. B 729 (1999) 297-305.
6. F. A. Walker, U. Simonis, in: R. B. King (Ed.), Encyclopedia of Inorganic Chemistry, vol. 4, Iron Porphyrin Chemistry: John Wiley & Sons, New York, 1994, pp 1785-1846 and refs therein.
7. K. L. Brown, Chem. Rev. 105 (2005) 2075-2149.
8. A. W. Larkum, M. Kuhl, Trends Plant Sci. 10 (2005) 355-357.
9. P. Hambright, in: K. M. Kadish, K. M., Smith, K. M., Guilard, R. (Eds.). The Porphyrin Handbook, vol. 3, Water-Soluble Metalloporphyrins: Academic Press, N. Y. 2000, pp 129-210.
10. R. Bonnett, Chem. Soc. Rev. 24 (1995) 19-33.
11. M. R. Detty, S. L. Gibson, S. J. Wagner, J. Med. Chem. 47 (2004) 3897-3915.
12. B. Meunier, S. P. de Visser, S. Shaik, Chem. Rev. 104 (2004) 3947-3980.
13. J. T. Groves, K. Shalyaev, and J. Lee, in: K. M. Kadish, K. M., Smith, K. M., Guilard, R. (Eds.). The Porphyrin Handbook, vol. 4, Oxometalloporphyrins in Oxidative Catalysis: Academic Press, N. Y. 2000, pp 17-40.
14. J. T. Groves, Ann. N. Y. Acad. Sci. 47 (1986) 99-107.
15. I. Spasojevic, I. Batinic-Haberle, Inorg. Chim. Acta. 317 (2001) 230-242.
16. G. Ferrer-Sueta, C. Quijano, B. Alvarez, R. Radi, Methods Enzymol. 349 (2002) 23-37.
17. G. Ferrer-Sueta, D. Vitturi, I. Batinic-Haberle, I. Fridovich, S. Goldstein, G. Czapski, R. Radi, J. Biol. Chem. 278 (2003) 27432-27438.
18. N. Jin, J. L. Bourassa, S. C. Tizio, J. T. Groves, Angew. Chem. Int. Ed. 39 (2000) 3849-3851.
19. A. Robert, B. Loock, M. Momenteau, B. Meunier, Inorg. Chem. 30 (1991) 706-711.
20. M. Matsu-ura, F. Tani, S. Nakayama, N. Nakamura, Y. Naruta, Angew. Chem. Int. Ed. 39 (2000) 1989-1991.
21. J. P. Collman, A. S. Chien, T. A. Eberspacher, J. I. Brauman, J. Am. Chem. Soc. 122 (2000) 11098-11100.
22. X. F. Li, J. Y. Liu, Z. X. Guo, Y. Z. Li, A. J. Huang, W. B. Chang, Chin. Chem. Lett. 12 (2001) 979-982.
23. N. Safari, F. Bahadoran, M. R. Hoseinzadeh, R. Ghiasi, J. Porphyrins Phthalocyanines 4 (2000) 285-291.
24. K. Wietzerbin, J. Bernadou and B. Meunier, Eur. J. Inorg. Chem. (1999) 1467-1477.
25. F. Cui, Dolphin, Can. J. Chem. 70 (1992) 2314-2318.
26. J. T. Groves, T. E. Nemo, R. S. Myers, J. Am. Chem. Soc. 101 (1979) 1032-1033.
27. T. Nakano, N. Agatsuma, S. Kodama, H. Kakuda, D. Dolphin, Bull. Chem. Soc. Jpn. 69 (1996) 3513-3521.
28. V. Karunaratne, D. Dolphin, Chem. Soc. Chem. Commun (1995) 2105-2106.
29. E. do Nascimento, G. de F. Silva, F. A. Caetano, M. A. M. Fernandes, D. C. da Silva, M. E. M. D. de Carvalho, J. M. Pernaut, J. S. Reboucas, Y. M. Idemori, J. Inorg. Biochem. 99 (2005) 1193-1204.
30. F. Cui, D. Dolphin, Can. J. Chem. 73 (1995) 2153-2157.
31. V. Karunaratne, D. Dolphin, Tetrahedron Lett 37 (1996) 603-604.
32. M. Perree-Fauvet, A. Gaudemer, J. Chem. Soc., Chem. Commun. (1981) 874-875.
33. I. Tabushi, N. Koga, J. Am. Chem. Soc. 101 (1979) 6456-6458.
34. I. Tabushi, A. Yazaki, J. Am. Chem. Soc. 103 (1981) 7371-7373.
35. D. Mansuy, M. Fontecave, J.-F. Bartoli, J. Chem. Soc. Chem., Commun. (1983) 253-254.
36. L.-N. Ji, M. Liu, A.-K. Hsieh and T. S. A. Hor, J. Mol. Catalysis A 70 (1991) 247-257.
37. E. I. Karasevich, Y. K. Karasevich, Kin. Catal. 41 (2000) 492-498.
38. E. I. Karasevich, Y. K. Karasevich, Kin. Catal. 41 (2000) 485-491.
39. J. Hart-Davis, P. Battioni, J.-L. Boucher, D. Mansuy, J. Am. Chem. Soc. 120 (1998) 12524-12530.
40. D. Mansuy, M. Fontecave, Biochem. Biophys. Res. Commun. 104 (1982) 1651-1657.
41. B. Halliwell, J. M. C. Gutteridge, Free Radicals in biology and Medicine, $3^{rd}$ ed., Oxford University Press, 1998.
42. I. Batinic-Haberle, L. Benov, I. Spasojevic, P. Hambright, A. L. Crumbliss, I. Fridovich, Inorg. Chem. 38 (1999) 4011-4022.
43. I. Batinic-Haberle, I. Spasojevic, R. D. Stevens, A. Okado-Matsumkoto, B. Bondurant, I. Fridovich, Z. Vujaskovic, M. W. Dewhirst, Dalton Trans. (2006) 617-624.
44. I. Spasojevic, I. Batinic-Haberle, I. Fridovich, Nitric Oxide: Biology and Chemistry 4 (2000) 526-533.
45. E. Jahde, M. F. Rajewski, Cancer Res. 42 (1982) 1505-1512.
46. M. Stubbs, P. M. J. McSheehy, J. R. Griffiths, C. L. Bashford, Mol. Med. Today 6 (2000) 15-19.
47. J. Morgan, D. S. Leake, FEBS Letters 333 (1993) 275-279.
48. C. Murdoch, A. Giannoudis, C. E. Lewis, Blood 104 (2004) 2224-2234.
49. I. Batinic-Haberle, I. Spasojevic, R. D. Stevens, P. Hambright, P. Neta, A. Okado-Matsumoto, I. Fridovich, I., J. Chem. Soc. Dalton Trans. (2004) 1696-1702.
50. O. Almarsson, T. C. Bruice, J. Am. Chem. Soc. 117 (1995) 4533-4544.
51. K. Murata, R. Panicucci, E. Gopinath, T. C. Bruice J. Am. Chem. Soc. 112 (1990) 6072-6083
52. R. Panicucci, T. C. Bruice, J. Am. Chem. Soc. 112 (1990) 6063-6071, 1990
53. H. Fujii, Coord. Chem. Rev., 2002, 226, 51-60.
54. B. Meunier, J. Bernadou, Top. Catal. 21 (2002) 47-54.
55. M. Newcomb, P. H. Toy, Acc. Chem. Res. 33 (2000) 449-455.
56. K.-F. Aguey-Zinsou, P. V. Bernhardt, J. J. De Voss, K. E. Slessor, Chem. Commun. (2003) 418-419.

57. W. J. Song, Y. O. Ryu, R. Song, W. Nam, J. Biol. Inorg. Chem. 10 (2005) 294-304.
58. W. Nam, Y. O. Ryu, W. J. Song, J. Biol. Inorg. Chem. 9 (2004) 654-660.
59. W. Nam, S. W. Jin, M. H. Lim, J. Y. Ryu, C. Kim, Inorg. Chem. 41 (2002) 3647-3652.
60. J. T. Groves, J. Inorg. Biochem. 100, (2006) 434-447.
61. N. B. J. Vollaard, B. J. Reeder, J. P. Shearman, P. Menu, M. T. Wilson, C. E. Cooper, Free Radic. Biol. Med. 39 (2005) 1216-1228.
62. G. Ferrer-Sueta, I. Batinic-Haberle, I. Spasojevic, I. Fridovich, R. Radi, Chem. Res, Toxicol. 12 (1999) 442-449.
63. Handbook of Chemistry and Physics, D. R. Lide, Ed., 74$^{th}$ edition, 1993-1994, CRC Press, Boca Raton.

The foregoing is illustrative of the present invention, and is not to be construed as limiting thereof. The invention is defined by the following claims, with equivalents of the claims to be included therein.

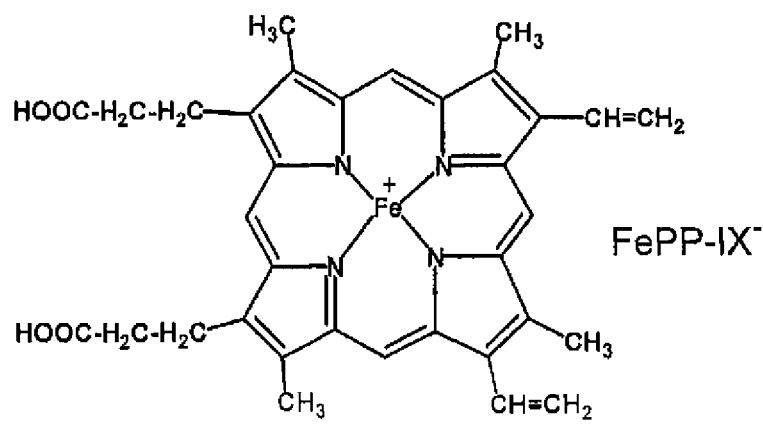

What is claimed is:

1. A method of treating a subject in need thereof with cyclophosphamide, the improvement comprising:
    concurrently administering said subject a metalloporphyrin in an amount effective to enhance the efficacy of said cyclophosphamide in said subject;
    wherein said metalloporphyrin comprises a transition metal(III)-substituted macrocyclic ligand complex containing a coordinated metal selected from the group consisting of iron, manganese, cobalt, nickel, ruthenium, and copper; and a pharmaceutically acceptable carrier;
    said subject having cancer, thrombotic thrombocytopenic purpura, Sjogren's syndrome, Reiter's syndrome, progressive systemic sclerosis, pemphigus, pemphigoid, necrotizing vasculitis, myasthenia gravis, multiple sclerosis, lupus erythematosus, sarcoidosis, granulomatosis, vasculitis, glomerulonephritis, chronic active hepatitis, ankylosing spondylitis, or Addison's disease.

2. The method of claim 1, said subject having a cancer selected from the group consisting of lung, colon, colorectal, liver, breast, prostate, ovarian, brain, and skin cancers or tumors.

3. The method of claim 1, said subject having Sjogren's Syndrome, myasthenia gravis, multiple sclerosis, lupus erythematosus, or Addison's disease.

4. The method of claim 1, wherein said metalloporphyrin is administered orally.

5. The method of claim 1, wherein said metalloporphyrin is administered parenterally.

6. The method of claim 1, wherein said cancer comprises a tumor and said metalloporphyrin is administered by injection directly into said tumor.

7. The method of claim 1, wherein
    said metalloporphyrin is Fe$^{III}$T(2,6-F$_2$-3-SO$_3$—P)P$^3$/Fe(III) meso tetrakis(2,6-difluoro-3-sulfonatophenyl)porphyrin; and
    said subject is afflicted with systemic lupus erythematosis.

* * * * *

UNITED STATES PATENT AND TRADEMARK OFFICE
CERTIFICATE OF CORRECTION

Page 1 of 2

PATENT NO.      : 8,759,324 B2
APPLICATION NO. : 13/763085
DATED           : June 24, 2014
INVENTOR(S)     : Spasojevic et al.

It is certified that error appears in the above-identified patent and that said Letters Patent is hereby corrected as shown below:

IN THE SPECIFICATION
Column 9, Lines 55-65: Please correct the Compound below:

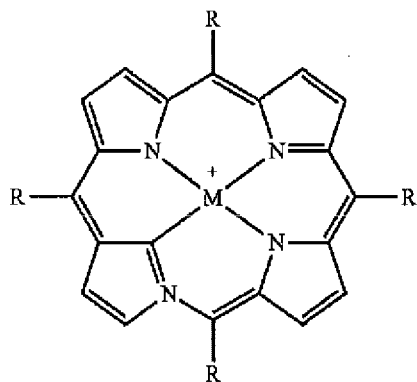

to read as:

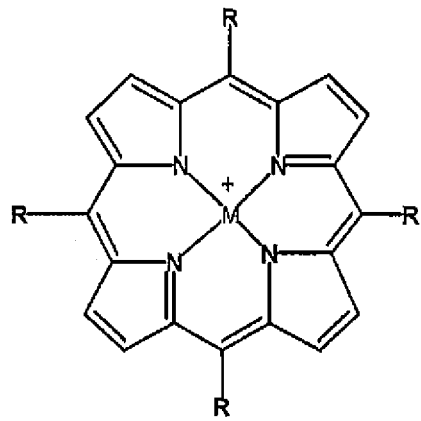

Signed and Sealed this
Twenty-third Day of February, 2016

Michelle K. Lee
*Director of the United States Patent and Trademark Office*

CERTIFICATE OF CORRECTION (continued)
U.S. Pat. No. 8,759,324 B2

IN THE SPECIFICATION
Column 10, Lines 2-14: Please correct the Compound below:

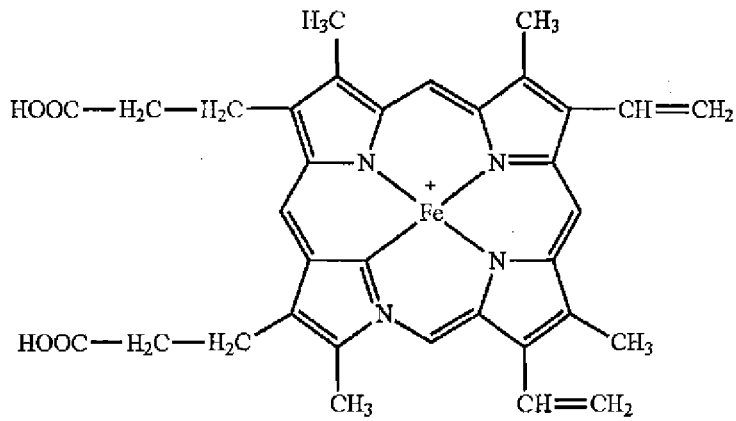

to read as: